(12) United States Patent
Levif et al.

(10) Patent No.: US 8,980,175 B2
(45) Date of Patent: Mar. 17, 2015

(54) METHODS FOR PLASMA STERILIZATION USING PACKAGING MATERIAL

(76) Inventors: Pierre Levif, Montréal (CA); Jacynthe Séguin, Saint-Lambert (CA); Michel Moisan, Outremont (CA)

( * ) Notice: Subject to any disclaimer, the term of this patent is extended or adjusted under 35 U.S.C. 154(b) by 144 days.

(21) Appl. No.: 13/813,948

(22) PCT Filed: Aug. 4, 2011

(86) PCT No.: PCT/CA2011/000887
§ 371 (c)(1),
(2), (4) Date: Feb. 2, 2013

(87) PCT Pub. No.: WO2012/016329
PCT Pub. Date: Feb. 9, 2012

(65) Prior Publication Data
US 2013/0136653 A1    May 30, 2013

Related U.S. Application Data

(60) Provisional application No. 61/371,429, filed on Aug. 6, 2010.

(51) Int. Cl.
| | |
|---|---|
| *A61L 2/00* | (2006.01) |
| *A62B 7/08* | (2006.01) |
| *B01J 19/08* | (2006.01) |
| *G01N 23/00* | (2006.01) |

(Continued)

(52) U.S. Cl.
CPC ............... *B65B 55/02* (2013.01); *B65B 55/18* (2013.01); *A61L 2/20* (2013.01)
USPC ... 422/24; 422/121; 422/186.04; 422/186.05; 422/186.07; 250/455.11; 250/461.1; 250/492.1

(58) Field of Classification Search
CPC ............... A61L 2/00; A61L 9/18; A61L 9/20
USPC ........... 422/24, 121, 186.04, 186.05, 186.07, 422/906; 250/455.11, 461.1, 492.1
See application file for complete search history.

(56) References Cited

U.S. PATENT DOCUMENTS

| | | | |
|---|---|---|---|
| 4,321,232 A * | 3/1982 | Bithell | ........................... 422/23 |
| 5,512,244 A | 4/1996 | Griffiths et al. | |

(Continued)

FOREIGN PATENT DOCUMENTS

| | | |
|---|---|---|
| WO | 02058746 | 8/2002 |
| WO | 2007047028 | 4/2007 |

OTHER PUBLICATIONS

Setlow, "Spores of *Bacillus subtilis*: their resistance to and killing by radiation, heat and chemicals", The Society for Applied Microbiology, Journal of Applied Microbiology 101 (2006) 514-525.

(Continued)

*Primary Examiner* — Monzer R Chorbaji
(74) *Attorney, Agent, or Firm* — Bereskin & Parr LLP/S.E.N.C.R.L., s.r.l.

(57) ABSTRACT

There are provided methods for sterilizing and/or disinfecting an object. The methods can comprise exposing the object disposed in a packaging material having at least one open end to an afterglow plasma, wherein the packaging material is non-porous and is transparent to UV radiation. There are also provided methods for using a packaging material. The methods can comprise disposing an object to be sterilized into the packaging material, the packaging material being non-porous, transparent to UV radiation, and having at least one open end; and exposing the object and the packaging material having at least one open end, to an afterglow of a plasma, thereby at least substantially protecting the object to be sterilized.

19 Claims, 8 Drawing Sheets

(51) Int. Cl.
  *G01N 21/64* (2006.01)
  *A61N 5/00* (2006.01)
  *B65B 55/02* (2006.01)
  *B65B 55/18* (2006.01)
  *A61L 2/20* (2006.01)

(56) References Cited

U.S. PATENT DOCUMENTS

| | | | |
|---|---|---|---|
| 7,700,039 B2 * | 4/2010 | Nagatsu | 422/21 |
| 2005/0067312 A1 | 3/2005 | Gupta et al. | |
| 2005/0268573 A1 | 12/2005 | Yan | |
| 2010/0178198 A1 | 7/2010 | Moisan et al. | |

OTHER PUBLICATIONS

Magge et al., "Analysis of dye binding by and membrane potential in spores of *Bacillus* species", The Society for Applied Microbiology, Journal of Applied Microbiology 106 (2009) 814-824.

Owens, "Estimation of the Surface Free Energy of Polymers", Journal of Applied Polymer Science, vol. 13, pp. 1741-1747 (1969).

Munakata et al., "Inactivation Action Spectra of *Bacillus subtilis* Spores in Extended Ultraviolet Wavelengths (50-300 nm Obtained with Synchrotron Radiation", Photochemistry and Photobiology vol. 54, No. 5, pp. 761-768, 1991.

Kinnari et al., "Effect of surface roughness and sterilization on bacterial adherence to ultra-high molecular weight polyethylene", Clin. Microbial Infect, 2009; 16: 1036-1041.

Gardner et al., "Introduction to sterilization and disinfection", Churchill Livinstone, 1986.

Levif et al., "Packaging materials for plasma sterilization with the flowing afterglow of an N2—O2 discarge: damage assessment and inactivation efficiency of enclosed bacterial spores", J. Phys. D: Appl. Phys. 44 (2011) 405201 (13pp).

* cited by examiner

METHODS FOR PLASMA STERILIZATION USING PACKAGING MATERIAL

CROSS-REFERENCE TO RELATED APPLICATIONS

This application is a 35 USC 371 national stage entry of PCT/CA2011/000887 filed on Aug. 4, 2011 and which claims priority from U.S. provisional application No. 61/371,429 filed on Aug. 6, 2010. These documents are hereby incorporated by reference in their entirety.

FIELD OF THE DISCLOSURE

This disclosure relates to the field of sterilization using species generated by a plasma (ionized gas). More particularly, it relates to carrying out plasma sterilization using a packaging material.

BACKGROUND OF THE DISCLOSURE

Today, several types of medical objects are distinguished by their composition (metal, glass, polymer). Knowing that the temperature of polymers must not exceed about 60-70° C. (for the least resistant), consequently, it is necessary to use another method than the one based on heat (autoclave, etc.) to sterilize them.

Ethylene oxide (EtO) is a good candidate for sterilizing polymers. The sterilization cycle in this case includes 2-4 hours of contact with EtO and a long ventilation period (at least 12 hours) because of EtO toxicity. (J. F. Gardner and M. M. Peel, *Introduction to Sterilization, Disinfection and Infection Control*, Churchill Livingstone, Melbourne Edinburgh London Tokyo and New York, 1991).

The use of a $N_2$—$O_2$ flowing afterglow is an alternative solution of choice for EtO sterilization of polymers because it does not seem to generate long-lived toxic by-products. Also, the Applicants found no impregnation of residues/toxic materials on polymers such as polyethylene and polystyrene. Therefore, no ventilation period is needed and, as a result, the duration of the whole sterilization cycle would be shorter.

To ensure that the objects remain sterile, these are generally packaged or wrapped before the sterilization cycle. There are various types of packaging according to the sterilization method.

To the best of the knowledge of the Applicants, the literature does not contain any guideline regarding specific packaging for medical devices and other objects when using the flowing afterglow of a $N_2$—$O_2$ plasma.

SUMMARY OF THE DISCLOSURE

According to one aspect, there is provided a method for sterilizing and/or disinfecting an object comprising exposing the object disposed in a packaging material having at least one open end or at least one portion comprising an aperture, to an afterglow plasma, wherein the packaging material is non-porous and is transparent to UV radiation.

According to another aspect, there is provided a method for using a packaging material, the method comprising:

disposing an object to be sterilized into the packaging material, the packaging material being non-porous, transparent to UV radiation, and having at least one open end or at least one portion comprising an aperture; and exposing the object and the packaging material to an afterglow of a plasma, thereby lowering the potential level of damage imparted to the object to be sterilized by the afterglow.

According to another aspect, there is provided a method for using a packaging material, the method comprising:

disposing an object to be sterilized into the packaging material, the packaging material being non-porous, transparent to UV radiation, and having at least one open end or at least one portion comprising an aperture; and exposing the object and the packaging material to an afterglow of a plasma, thereby at least substantially protecting the object to be sterilized.

According to another aspect, there is provided a method for using a packaging material, the method comprising:

inserting an object to be sterilized into the packaging material, the packaging material being non-porous, transparent to UV radiation, and having at least one open end or at least one portion comprising an aperture; and exposing the object and the packaging material to an afterglow of a plasma, thereby protecting the object to be sterilized without significantly reducing efficiency of sterilization as compared to a same treatment carried out outside of the packaging material.

It was found by Applicants that these methods are very efficient for plasma sterilization and/or disinfection. It was also found that when a given packaging material is used to insert therein the object to be treated, the object can be sterilized and/or disinfected without significant damage. In fact, it was observed that by using such a packaging material, having at least one open end or at least one portion having an aperture, the treated object does not appear to lose its properties. When the same treatment is applied to an object that is not disposed into such a packaging material as those used in the methods of the present disclosure, the latter could be significantly modified as compared to when the object is inserted into such a packaging material, based on a first examination by a naked eye.

The packaging material used can be non-porous and transparent to UV radiation. With the non-porous material tested, sealing or closing can be effected once the object has been sterilized. The non-porous feature can also allow the treated object in the packaging material to remain sterile for a long period of time (at least one month). It was also found that such methods involving a packaging material that is transparent to UV is very efficient for the following reasons, without the Applicants being bound by such explanations: 1) since UV transparency allows for UV photons outside the packaging to penetrate into it, these photons contribute to inactivate microorganisms therein and more particularly when UV radiation intensity is for example maximized; 2) UV transparency of the packaging to UV photons implies very little interaction of these photons with the material, and thus little or substantially no damage to it; 3) some of the UV photons that have penetrated the packaging material could participate in regenerating N and O atoms (through dissociation of $N_2$ and $O_2$ molecules), followed by the reforming of NO excited molecules that will emit UV photons.

Using such methods, in which the object is disposed in the packaging material having at least one open end or at least one portion comprising an aperture, prevents the packaging material to collapse on the object or inflate (possibly blow up) in view, for example, of the difference of pressure before, during and after the sterilization process. Therefore, this also prevents ripping the packaging material and allows for maintaining the object sealed under sterile conditions into the packaging material.

BRIEF DESCRIPTION OF THE FIGURES

Further features and advantages of the disclosure will become more readily apparent from the following description of various embodiments as illustrated by way of examples in the appended figures wherein:

FIG. 6 (a) shows a digital image of non-exposed B. atrophaeus spores, DAPI colored, obtained with an optical fluorescence microscope;

FIG. 6 (b) shows a digital image (obtained with an optical fluorescence microscope) of B. atrophaeus spores exposed to the $N_2$—$O_2$ flowing afterglow, without packaging material, for 60 minutes, then DAPI colored, according to an example of a method according to the present disclosure;

FIG. 6 (c) shows a digital image (obtained with an optical fluorescence microscope) of B. atrophaeus spores exposed to the $N_2$—$O_2$ flowing afterglow, inside a packaging material, for 120 minutes, then DAPI colored, according to an example of a method according to the present disclosure;

DETAILED DESCRIPTION OF THE DISCLOSURE

The following examples are presented in a non-limitative manner.

The expression "non-porous" as used herein refers, for example, to a material that does not allow passage of gas or of liquid through it, indicating that it lacks pores or interstices.

The expression "impervious to microorganisms" as used herein refers, for example, to a material that is incapable of being penetrated because it is non-porous. Unless in direct contact with culture nutrients, a bacteria cannot proliferate because of the absence of diffusion of nutrients through the material, as demonstrated further on in the present disclosure by using, for example, a solid-culture medium (nutrient agar). Because it is non-porous and impervious to bacteria, it can remain in such a condition for a period of time up to about 1, 2, or 3 years. For example, it can stay in such a condition for a period of time up to about 3 years.

The expression "transparent to UV radiation" as used herein refers, for example, to a material that is transparent to UV radiation at such an extent that the material is at least substantially prevented from being damaged by the UV radiation. For example, such a material has a transmission of at least 70% at a wavelength λ of 300 nm and a transmission of at least 80% at a wavelength λ of 400 nm. Such a material transparent to UV radiation can also have a transmission of at least 25% at a wavelength λ of 200 nm.

The expression "at least substantially prevented from being damaged by afterglow species (UV radiation and particles)" as used herein refers, for example, to the fact that once exposed to the afterglow, the packaging material will not lose more than 30, 25, 20, 15, 10 or 5% of its non-porosity and initial transparency to UV radiation.

The expression "lowering the potential level of damage imparted to the object to be sterilized by the afterglow" as used herein refers, for example, to the fact that once exposed to the afterglow, the object to be sterilized will not lose more than 30, 25, 20, 15, 10 or 5% of its original characteristics such as fo example mass, contact angle value.

The term "disinfection" or "disinfecting" as used herein refers, for example, to the inactivation of at least 3 log of microorganisms on a total amount of about $10^6$ or more microorganisms.

The term "high level disinfection" as used herein refers, for example, to inactivation of at least 4 to 5 log of microorganisms on a total amount of about $10^6$ or more microorganisms.

The term "sterilization" or "sterilizing" as used herein means, for example, to inactivate at least 6 log of microorganisms on a total amount of $10^6$ or more microorganisms.

The term "inactivating" or the expression "to inactivate" as used herein refers, for example, to render the microorganisms unable to grow/replicate.

The expression "dry ozone" as used herein refers, for example, to gaseous ozone with a relative humidity (RH) of less than about 40%, or less than about 2% (determined with a hygrometer).

The expression "humidified ozone" as used herein refers, for example, to gaseous ozone with a relative humidity of more than about 2%, generally about 40% to about 80% RH, about 50% to about 75% RH, or about 65% to about 75% RH.

The expression "without significantly reducing efficiency of sterilization as compared to a same treatment carried out outside of the packaging material" as used herein refers, for example, to a method that does not reduce the efficiency of the sterilization, inactivation and/or disinfection by more than 5, 10, or 15%. For example, the efficiency can be about the same or does differ by less than 10 or 5%. For example, such an efficiency can be determined from a microorganism survival curve.

For example, the packaging material can be adapted to maintain at least 70, 75, 80, 85, 90, 95, 96, 97, 98, 99 or 99.5% of its initial non-porosity and initial transparency to UV radiation after exposure to the afterglow.

For example, the packaging material can be impervious to bacteria.

For example, the packaging material can be adapted to maintain at least 70, 75, 80, 85, 90, 95, 96, 97, 98, 99 or 99.5% of its imperviousness to microorganisms after exposure to the afterglow. For example, the microorganisms can be bacteria.

For example, the packaging material can be in the form of a pouch having one open end or a bag having one open end.

For example, the packaging material can be in the form of a container.

For example, the packaging material can comprise a polyolefin polymer. The polyolefin polymer can comprise polymerized ethylene monomers, polymerized propylene monomers, or a mixture thereof. The packaging material can comprise a high density polyethylene-based polymer, or a low density polyethylene-based polymer. It can also comprise a polypropylene-based polymer or an ethylene-propylene copolymer.

Other packaging materials can also be considered besides polymers. For example, fused silica as well as other types of materials can be used. A container made from fused silica can be used since it has a good transparency to UV radiation starting at approximately 180 nm (the lower portion of the NO (gamma) molecular system), it is non-porous and, instead of thermal sealing, one could cap it once the sterilization process is over. The walls of the container (for example a vial) (as that of all packaging materials) can be as thin as possible not to reduce significantly the UV photons coming from the flowing afterglow.

Figure 4:
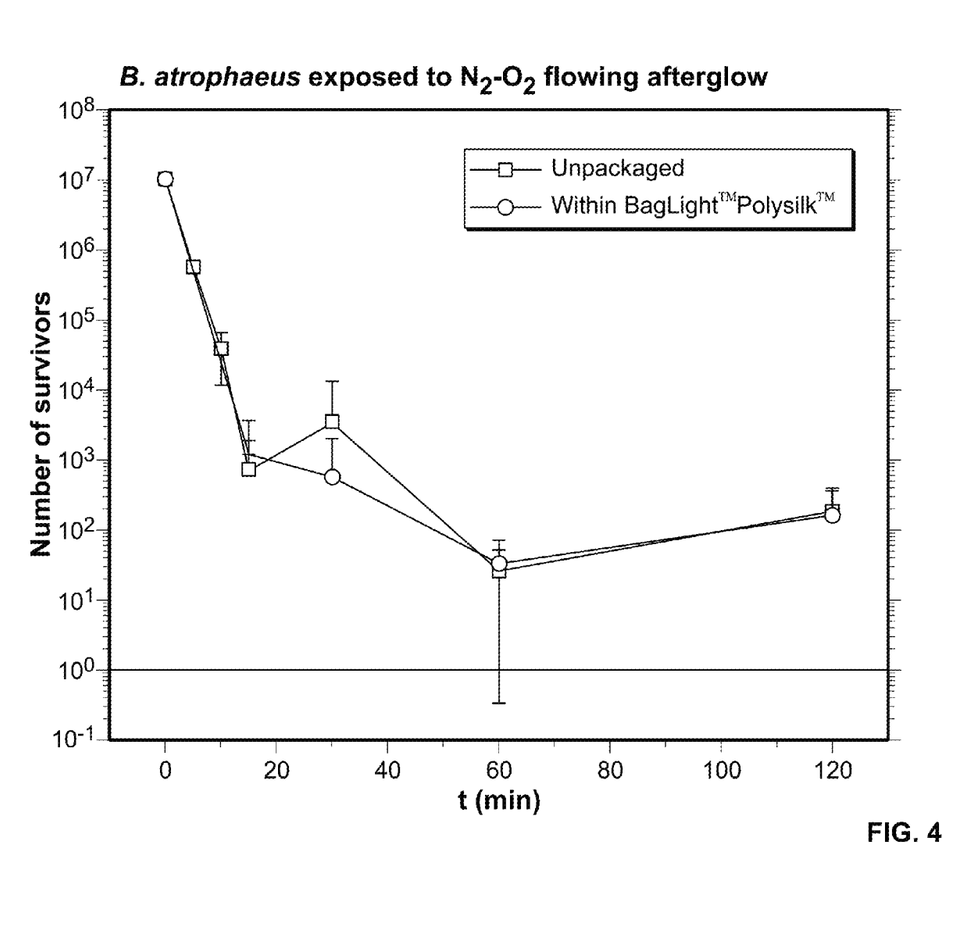
FIG. 4 shows survival curves for $10^7$ B. atrophaeus spores initially deposited in (polystyrene) Petri dishes exposed to an $N_2$—$O_2$ discharge (plasma) flowing afterglow, with and without the packaging material, in accordance with an example of a method of the present disclosure.

The packaging material can be a material that has a degree of surface (heterogeneous) recombination of N into $N_2$ and of O into $O_2$ on the packaging material that is low as possible. This effect is illustrated in FIG. 4 from the article of Levif et al. <<Packaging materials for plasma sterilization with the flowing afterglow of an $N_2$—$O_2$ discharge: damage assessement and inactivation efficiency of enclosed bacterial spores" in Journal of Physics D: Applied Physics, 44, 2011, 40511. It is assumed, without being bound to such a theory, that the lower the degree of heterogeneous recombination, the higher the density of NO (excited) molecules formed (greater number of N and O atoms available), thus the higher the number of UV photons created in the chamber (outside the packaging material), and consequently the faster the sterilization process. Fused silica is known to have a probability of surface recombination of N and O atoms (into their original molecules) to be less than $10^{-3}$.

Various ways of ensuring the penetration of the particles of the afterglow as the sterilization process begins and goes on can be achieved: e.g. a small aperture (for example a hole or circular hole) (for example few mm in diameter) could be provided on the packaging material (for example pouch). This hole could be simply patched or closed (no thermal sealing) once the sterilization process is over.

For example, the packaging material was found not to be toxic on human cells, as determined in accordance with ANSI/AAMI/ISO 10993:2003.

According to one embodiment, the plasma can be produced by subjecting a liquid or gas to an electric field. For example, the gas can be subjected to the electric field, the gas comprising at least one component chosen from $O_2$, $N_2$, Ne, Ar, Kr, Xe, He, O, CO, $CO_2$, $N_2O$, NO, $NO_2$, $NO_3$, air, synthetic air, and mixtures thereof. The gas can also comprise $N_2$ and $O_2$. For example, the gas can comprise about 0.01 to about 20.0, 0.1 to about 20, about 0.1 to 2, about 0.5 to 1%, or about 0.1 to 1% of $O_2$.

For example, the gas can be provided by a $N_2$ flow rate of about 600 to about 2000 sccm and an added $O_2$ flow rate of about 1 to about 40 sccm. The gas can also be provided by a $N_2$ flow rate of about 800 sccm and an added $O_2$ flow rate of about 3 sccm.

According to one embodiment, the method can be carried out in a chamber having a volume of about 3 to about 8 L or about 6 L.

For example, the pressure in the chamber can be about 3 to about 7 Torrs or about 5 Torrs.

For example, the plasma can be generated by using an excitation frequency of about 433 MHz to about 3 GHz, about 915 MHz, or about 2.45 GHz.

For example, the method can be carried out with a power absorbed by the plasma source P (W) referred to the afterglow chamber volume V (L) of about P/V of 2 to about 40 W/L. The method can also be carried out with a power absorbed by the plasma source P (W) referred to the afterglow chamber volume V (L) of about P/V of about 20 W/L.

According to one embodiment, a gas is subjected to the electric field, the gas comprising Ar.

For example, the method can be carried out by maximizing intensity of UV radiation emanating from the $NO_y$ molecular system having a spectral domain of about 180 nm to about 290 nm or about 205 nm to about 290 nm.

For example, the afterglow plasma can be ozone in the form of the flowing afterglow of an $O_2$ corona discharge (or other mixtures containing $O_2$, e.g. air). The ozone can be dry ozone or humidified ozone.

The method can be carried out by maximizing UV radiation.

For example, the method can be carried out by:

measuring at least one of UV emission intensity and optical absorption to determine a density of states (or population density) of species emitting UV photons in the chamber as a function of gas pressure and gas flow rate to determine operating conditions that maximize UV radiation intensity and that maximize the presence of UV photon emitting species in the chamber; and applying the operating conditions in the chamber that maximize UV radiation intensity and that maximize the presence of UV photon emitting species in the chamber.

For example, the method can be carried out by:

measuring at least one of UV emission intensity and optical absorption to determine the population density of species emitting UV photons in the chamber as a function of gas pressure to determine a gas pressure that maximizes UV radiation intensity and that maximizes the presence of UV photon emitting species in the chamber;

measuring at least one of UV emission intensity and optical absorption to determine the population density of species emitting UV photons in the chamber as a function of the stream flow rate to determine a flow rate that maximizes UV radiation intensity and that maximizes the presence of UV photon emitting species in the chamber; and applying the stream at a flow rate and a gas pressure in the chamber that maximize UV radiation intensity and that maximize the presence of UV photon emitting species in the chamber.

For example, the method can be carried out by:

measuring at least one of UV emission intensity and optical absorption to determine the population density of species emitting UV photons in the chamber as a function of power density P/V to determine operating conditions that maximize UV radiation intensity and that maximize the presence of UV photon emitting species in the chamber; and applying the operating conditions in the chamber that maximizes UV radiation intensity and that maximizes the presence of UV photon emitting species in the chamber.

For example, exposition to the afterglow of the plasma can be carried out under vacuum or reduced pressure (typically below 10 Torrs).

For example, the method can be carried by maintaining the temperature of the object at a temperature below 80, 75, 70, 65, 60, 55, 50, 45, or 40° C.

For example, the packaging material can be disposed, in a sterilizer or chamber, in such a manner to be opposite to a plasma source or plasma inlet of the sterilizer.

For example, the packaging material can comprise a single open end that is disposed, in a sterilizer or chamber, in such a manner to be opposite to a plasma source or plasma inlet of the sterilizer.

For example, the method can be carried out in a sterilizer and wherein after exposure to the afterglow plasma and before opening the sterilizer, the at least one open end or the aperture of the at least one portion is closed.

For example, the at least one open end or the aperture of the at least one portion is thermally sealed under sterile conditions into the packaging material.

For example, the at least one open end or the aperture of the at least one portion can be closed or patched under sterile conditions into the packaging material.

Materials and Methods

Selection of a Packaging Material Compatible with Plasma Exposure and its Characterization after Exposure Various tests have been made in order to identify different suitable packaging materials to be used with the methods previously described.

The study was conducted using a small-volume sterilizer (6 L) in a $N_2$—$O_2$ flowing afterglow mode.

Figure 1:
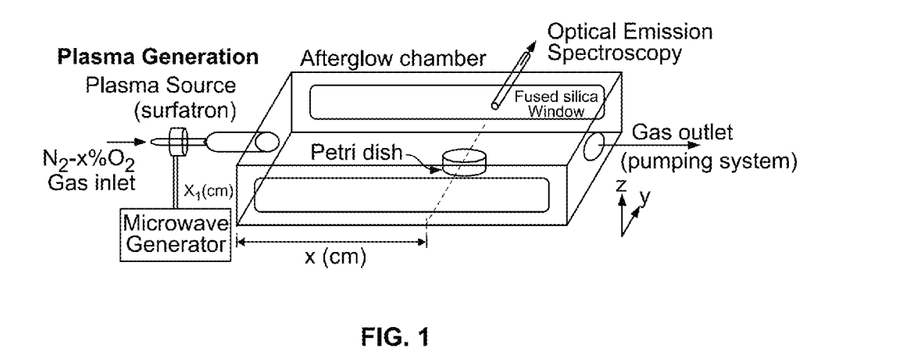
FIG. 1 shows a schematic representation of sterilizer operated in a $N_2$—$O_2$ flowing afterglow (plasma post-discharge) mode used according to an example of a method of the present disclosure.
Figure 2:
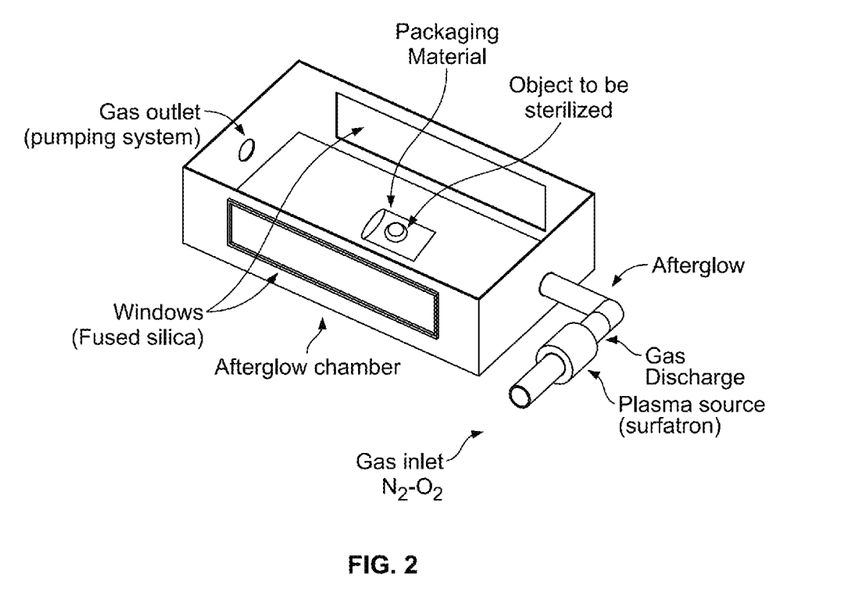
FIG. 2 shows another example of a sterilizer operated in a $N_2$—$O_2$ flowing afterglow (plasma post-discharge) mode used according to the present disclosure.

FIGS. 1 and 2 show two schematic representations of two examples of sterilizers used during experiments of the present disclosure. The sterilizers comprise a surfatron (high-frequency field applicator) plasma source, powered by a microwave generator (2.45 GHz operating frequency), and a chamber with a 6 L capacity in which the Applicants have placed the equipment to be sterilized. The plasma gas used was a mixture of dinitrogen ($N_2$) and dioxygen ($O_2$). As it can be seen in FIG. 2, the open end (or aperture) is disposed in such a manner to be opposite to the inlet of the afterglow plasma in the sterilizer.

Results obtained with various packaging materials that are used in the medical field for sterilization purposes are discussed below.

The following packaging materials have been tested:

SteriPouch™ (CROSSTEX™) (generally used for sterilization with an autoclave (water vapor/steam);

Tyvek™ (generally used for sterilization with ethylene oxide and the Sterrad™ process);

Kimguard™ (Kimberley-Clark™) (generally used for sterilization with ethylene oxide and autoclave); and Polyethylene terephthalate films (PET), 12 μm thick, with pores of 10 nm (it4ip company, Belgium);

Various plastic films (PVC, polyethylene . . . ), which are commonly used in the food sector, such as for instance Saran-Wrap™ and ZipLock™.

In gas mixture and pressure conditions that have been set to maximize the intensity of UV radiation, Applicants could not obtain sterility with the SteriPouch®, the Tyvek® packaging materials or with the plastic films. These packaging materials showed, by visual inspection, apparent macroscopic modifications after at least 1 hour of exposure.

As for Kimguard™, Applicants observed a bacterial load reduction of a little more than 3 log over 1 hour (a reduction of 6 log is necessary to reach the sterility assurance level). This packaging material showed considerable degradation visible macroscopically. In addition, its mass has diminished by at most 3% after exposure and there was a loss of coloration of the packaging material. In the exposed polystyrene Petri dish, the Applicants found a lasting presence of a whitish material, coming from the packaging material. A microscopic analysis of the packaging material showed a strong deterioration of the polyethylene fibers of the material, which results in an ineffective antimicrobial barrier.

Macroscopic damaging of the packaging Kimguard™ materials (e.g. ripping) was most likely due to its exposure to the flux of reactive species present in the flowing afterglow (atomic oxygen O and/or metastable nitrogen $N_2$, and ions) and/or due to a heat flux.

All packaging materials mentioned above have been considered incompatible by the Applicants for plasma sterilization (and more particularly for $N_2$—$O_2$ afterglow or post-discharge), and not all for the same reasons. The UV transparency from 190 to 400 nm of Tyvek®, SteriPouch®, and KimGuard® was found by measurements to be below 2%.

Applicants unexpectedly found a polyolefin polymer packaging material (for example BagLight™PolySilk™ from Interscience™) that showed promising results. This material is described by the manufacturer as being olefins resulting essentially from the polymerization of ethylene and/or propylene. It can comprise a low density or a high density polyethylene polymer. For example, this material can further comprise additives such as catalysts (for example metallocene), antioxidants, etc.

Figure 3:
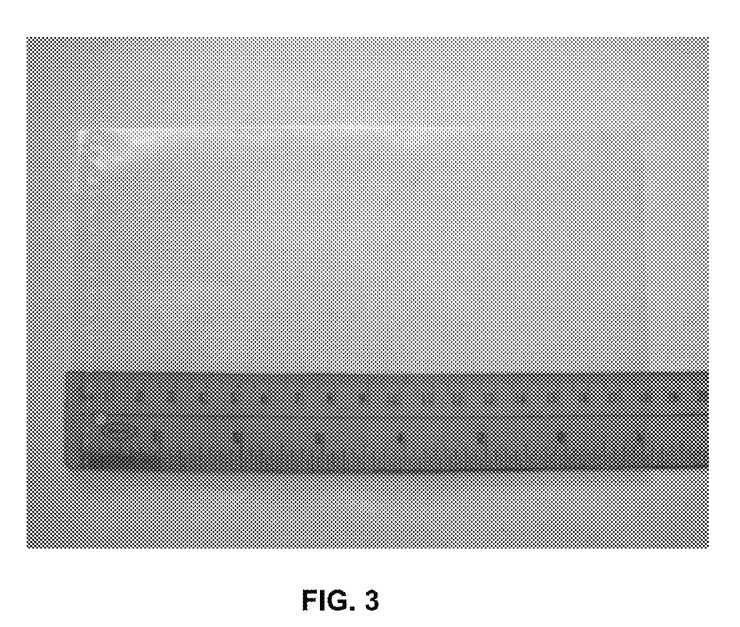
FIG. 3 is a photograph of an example of an untreated packaging material (with a volume capacity of 100 mL), which can be used carrying out an example of a method according to the present disclosure, showing that the packaging material is made from the same material on both sides and is highly transparent.

The polyolefin polymer packaging material (for example BagLight™PolySilk™) (see FIG. 3), used in the present experiments, had a volume capacity of 100 mL, a thickness of 70 μm, dimensions of 11 cm×18.5 cm and had an average weight of 2.880 g±0.005. Applicants have observed that there can be a maximum variation in mass of about 20% between the batches of packaging materials, which has been confirmed by the company. FIG. 3 shows, as an example of this packaging material, a photograph of the bag as sold where the left end of this packaging bag or pouch is (thermally) sealed and the right end is open.

The polyolefin polymer packaging material is sold as sterile bags (following gamma irradiation). It is delivered with a sterilization certificate and an expiration date (sterility guaranteed for 3 years). In addition, the packaging material is readily available for various volume capacities (e.g. 100, 400 and 3500 mL) depending on the intended applications. The company also offers a device for thermal sealing of the packaging materials.

First of all, Applicants verified whether introducing or not the Petri dish in the packaging material before exposure to the afterglow had an impact on the inactivation kinetics of the bacterial spores (microbiology). Applicants have also characterized the physical properties of the packaging material before and after exposure to the $N_2$—$O_2$ flowing afterglow.

Microbiology

Survival Curves

Inactivation performances of the sterilizer have, amongst others, been evaluated on the basis of survival curves of *B. atrophaeus* bacterial spores ATCC™9372. The microorganisms, $10^7$ suspended in 200 μl of water, were deposited in polystyrene Petri dishes (Sarstedt, 83.1801, 60×15 mm) and the deposits were dried at ambient temperature and protected from light.

The Petri dishes were arranged in the center of the chamber and were exposed with and without the packaging material. As applicable, the Petri dish is placed inside the packaging material, which is not closed during exposure.

Conditions effective for maximizing the intensity of the UV radiation emanating from the $NO_y$ molecular system (spectral domain: 205 nm-290 nm) were found to be the following: a $N_2$ flow rate of 800 standard cm³/min (sccm) with an addition of 3 sccm of $O_2$ for a final $O_2$ concentration of 0.37% in the $N_2$—$O_2$ mixture. Pressure in the afterglow chamber was 5 Torrs, the plasma-source excitation frequency being set at 2.45 GHz and the measured power absorbed by the plasma yielded 105 W (when power is expressed with respect to the afterglow chamber volume it gives P/V=17.5 W/L).

The survival curves obtained with and without the packaging material are displayed in FIG. 4. These results allow to check by comparison whether the polyolefin polymer packaging material has a direct effect on the inactivation of $B.$ $atrophaeus$ bacterial spores. The results were obtained from several independent experiments, performed in at least duplicates using different spore stocks.

FIG. 4 shows the survival curves for $B.$ $atrophaeus$ spores exposed to the $N_2$—$O_2$ flowing afterglow, the Petri dishes being exposed with or without packaging material. Applicants observed that, with and without the packaging material, evolution of the number of survivors with exposure time was very similar. This lets the Applicants presume, without being bound by this theory, that the presence of the packaging material (open at one end) does not interfere with the inactivation mechanism(s).

Applicants have checked the impact of the vacuum effect on microorganism inactivation. In order to do so, the polystyrene Petri dish containing the $B.$ $atrophaeus$ spores was placed inside the polyolefin polymer packaging material, then positioned in the middle of the chamber. Vacuum in the chamber was achieved using a primary-vacuum pump for 30 minutes. The recovered spores culture after the vacuum process, showed that the vacuum did not have any effect on the viability of the bacterial spores. Indeed, Applicants recovered $10^7$ spores, which is the number of viable spores that was initially deposited.

It is to be noted that Applicants are using $B.$ $atrophaeus$, a validated biological indicator for conventional sterilization systems and one of the most resistant reference bacterial endospores under their experimental conditions (desiccation and UV irradiation). Prior art documents related to plasma sterilization often refer to the use of the $Geobacillus$ $stearothermophilus$ spore, which the Applicants found to be less resistant under their operating conditions.

Antimicrobial Barrier of Packaging Material

Applicants have checked the integrity (condition state) of the antimicrobial barrier after exposure to the plasma.

Applicants have evaluated the external surface of the polyolefin polymer to determine whether it is an effective antimicrobial barrier, before and after exposure to the $N_2$—$O_2$ flowing afterglow. Qualitative experiments with bacterial cultures were made as follows: a deposit of $10^6$ spores in 10 µl of $H_2O$ was made and allowed to dry onto coupons (3 cm×3 cm) coming from the non-exposed packaging material (control) and from the material exposed for 120 min to the $N_2$—$O_2$ flowing afterglow. These coupons were then put 1), with their face without deposit, on a solid culture medium, being Trypticase Soy Agar (TSA). At the same time another series of coupons were placed 2) with their deposit in direct contact with the TSA. Growth was then evaluated after incubation at a temperature of 37° C. for 24 hrs.

This allowed to check 1) whether the bacteria that are not in direct contact with the culture medium could go through BagLight™PolySilk™ unexposed material and exposed material to the afterglow, and growth be detected on the other side. The deposit placed in direct contact with the culture medium 2) would inform on the inhibitory effect of the material, exposed or non-exposed if any.

The results were as follows. When the deposit was not in contact with the agar, whether the sample has been exposed or not to the afterglow, there was no bacterial proliferation on the coupons. On the other hand, when the dried deposits on the coupons were in direct contact with agar, there was a level of growth comparable for all coupons.

From this, Applicants were able to conclude that the non-porous nature of the polyolefin polymer packaging material was maintained after the $N_2$—$O_2$ afterglow and, furthermore, that this material had no sporicidal effect.

To determine whether the packaging material, unexposed or after exposure to the afterglow, has an impact on the growth of spores, Applicants inoculated $10^6$ spores in 5 ml liquid culture medium of Trypticase Soybean Broth (TSB) in the presence of coupons exposed for 120 min to the afterglow. The cultures were made using polystyrene plates (6 wells), in triplicate. After 24 hours and, then, after 4 days of incubation at 37° C., the growth levels were evaluated by reading the optical density (OD) at the wavelength $\lambda$=405 nm, and compared with the OD of the spore culture without coupon. The results are obtained from a statistic average and are presented in Table 1.

TABLE 1

Spore growth in liquid culture nutritive medium in the presence of coupons cut from the packaging material and exposed to the afterglow.

| | OD reading at $\lambda$ = 405 nm | |
| --- | --- | --- |
| | After 24 h incubation | After 4 days of incubation |
| No coupon in the culture | 0.642 ± 0.027 | 0.940 ± 0.040 |
| With coupons exposed to the afterglow | 0.820 ± 0.017 | 1.450 ± 0.080 |

The coupon exposed to the afterglow shows no inhibition of spore germination nor of outgrowth Evaluation of Growth and of Biofilm Formation by the $Staphylococcus$ $aureus$ Bacterium LSPQ 2520.—in Presence of the Polyolefin Polymer Packaging Material Applicants have also evaluated the capacity of biofilm formation and growth by $S.$ $aureus$ bacteria on the packaging material. The procedure was undertaken by inoculating $10^6$ bacteria in 5 ml of liquid culture medium (Trypticase Soybean Broth (TSB) containing 1% glucose) and culturing in 6 wells polystyrene plates in presence of BagLight™PolySilk™ coupons, exposed for 120 min to the afterglow and unexposed ones. After 24 hours of incubation at 37° C., the growth levels were evaluated by reading the optical density (OD) at 620 nm. The $S.$ $aureus$ bacterium LSPQ 2520 is recognized for its ability to form a biofilm. Applicants have checked this property on the polyolefin polymer packaging material. After 4 days of culture, the coupons were removed, rinsed under running water to remove non-adherent bacteria, dried in open air and then colored with Crystal violet (a chemical product used for Gram stain). The dye is then extracted from the biofilm with a discoloration solution (40% methanol, 10% acetic acid, 50% $H_2O$). The OD of the extracted coloring agent is read at $\lambda$=570 nm and represents a semi-quantitative measurement of the biofilm mass. Comparison of growth levels and of biofilm mass formation by the bacteria on unexposed and on exposed coupons, are shown in Table 2.

TABLE 2

Growth of S. aureus bacteria and their biofilm formation determined in presence of exposed and unexposed coupons of the polyolefin polymer packaging material.

| | Growth (24 h) OD at $\lambda = 620$ nm | Biofilm formation (4 days) OD of extracted dye at $\lambda = 570$ nm | Ratio OD biofilm/OD growth |
|---|---|---|---|
| Non-exposed bag | 0.546 ± 0.15 | 0.667 ± 0.05 | 1.22 ± 0.42 |
| $N_2$—$O_2$ exposed bag | 0.519 ± 0.2 | 0.823 ± 0.06 | 1.59 ± 0.72 |

As for the *B. atrophaeus* spores, Applicants observed that, as displayed in Table 2, the coupons exposed to the afterglow have no inhibiting effect on the growth of *S. aureus* bacteria.

According to the results of Table 2, biofilm formation on the bag-coupon exposed for 120 min is somewhat more important than on a non-exposed bag (1.59/1.22=1.30 x). This indicates a modification of the surface of the bag following exposure which, without inhibiting growth, increases the biofilm mass.

Fluorescence Microscopy Using Fluorochrome 4',6'-diamidino-2-phenylindole (DAPI)

Figure 6A:
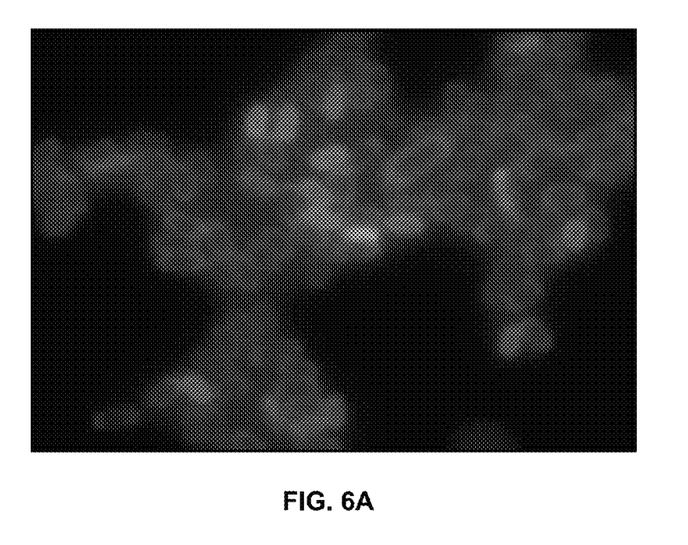
Figure 6B:
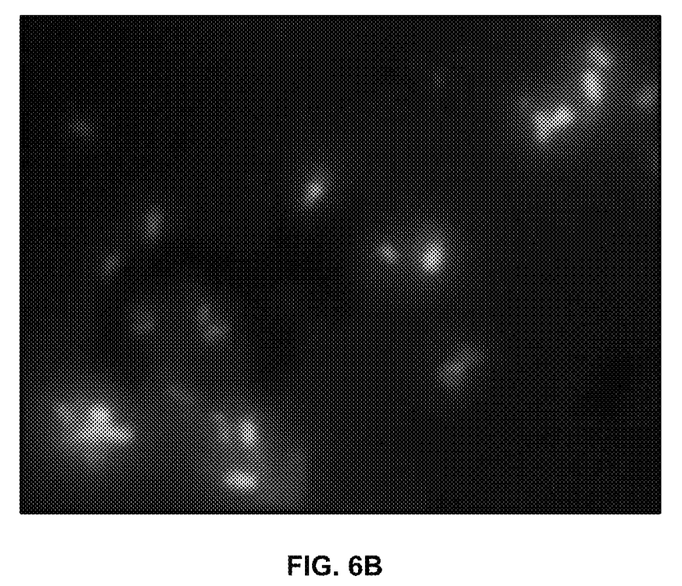
Figure 6C:
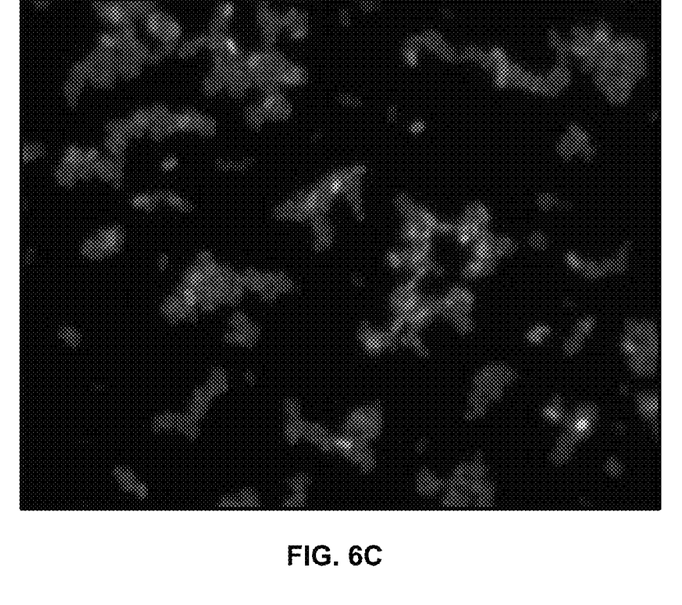

After having observed that the polyolefin polymer packaging material did not have an impact on spore inactivation mechanisms, Applicants have verified whether it had a protecting effect on the morphology of the bacterial spores deposited in polystyrene Petri dishes, enclosed in the packaging and subjected to the $N_2$—$O_2$ afterglow. To do so, Applicants employed a fluorescence microscopy technique that uses fluorochrome 4',6'-diamidino-2-phenylindole (DAPI) (DAPI, Product Information, SIGMA-ALDRICH). This chemical substance is generally used as a marker due to its capacity to emit fluorescent light after excitation. DAPI binds mainly to nucleic acids. In the case of bacterial spores, the dye has to penetrate the cell membranes and the cortex to reach the genetic material and bind to it. Photos taken with fluorescence microscope are presented in FIGS. 6 (*a*), 6 (*b*) and 6 (*c*).

Figure 5:
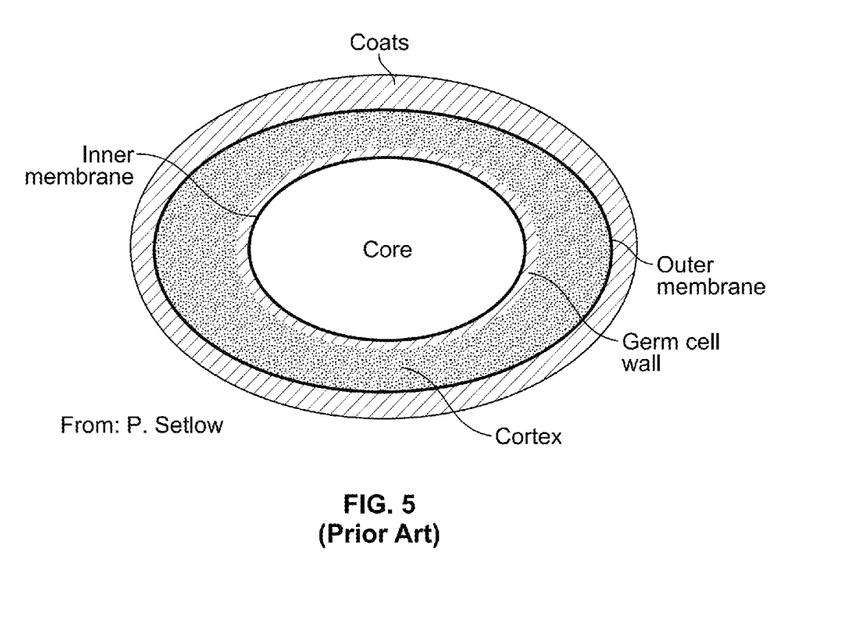
FIG. 5 (PRIOR ART) shows a diagram of the structure of a bacterial endospore.

The bacterial endospore is a dormant state of a vegetative cell. As such, it contains within, enclosed and protected by several coats, its genetic material (DNA and RNA) located in the core of the spore. These coats of protection are represented in FIG. 5. One of the particularities of the spore is its extreme resistance to chemical products (besides desiccation and irradiation), which is due in part to its outer membrane that does not let anything pass through and thus reach the core. For the DAPI to reach and attach to the DNA, there must be an integrity breakdown of the membranes before it can penetrate to the center or core of the spore.

The morphology of the spores exposed to afterglow, with and without bag, were evaluated with the DAPI according to the method proposed by the manufacturer (Example of its use can be found in: Analysis of dye binding by membrane potential in spores of *Bacillus* species, Journal of Applied Microbiology, 106, 814-824 (2009)). Our results are shown in FIGS. 6 (*a*), 6 (*b*) and 6 (*c*).

FIG. 6 (*a*) shows a digital image, obtained with an optical fluorescence microscope of non-exposed *B. atrophaeus* spores. Applicants note that the fluorescence occurred at the periphery of the spore, and not in its center, which implies that the DAPI was unable to go to its center or core.

FIG. 6 (*b*) shows a digital image of *B. atrophaeus* spores exposed to $N_2$—$O_2$ afterglow without packaging material for 60 minutes. Compared to FIG. 6 (*a*), Applicants noted that the fluorescence was more intense in the center or core of the spore, which indicates loss of spore membrane integrity, which allowed the DAPI to reach and bind to the genetic material.

FIG. 6 (*c*) shows a digital image of *B. atrophaeus* spores exposed to $N_2$—$O_2$ afterglow inside the polyolefin polymer packaging material for 120 minutes. Applicants noted, by comparing FIGS. 6 (*a*) and 6 (*b*), that the integrity of the spore was maintained.

Considering that the number of survivors was very similar for spores exposed with and without the packaging material to the $N_2$—$O_2$ afterglow (see FIG. 4), this led Applicants to conclude, without being bound to such an explanation, that the packaging material (while allowing for sterilization and/or disinfection) provided protection to the morphology of the spores. It also indicates that the integrity breakdown of the membranes does not contribute necessarily to the inactivation mechanism(s). This is an interesting point and shows, by extrapolation, the importance that the packaging material can have for the protection of the objects to be sterilized. The packaging material should therefore have a protective role for the objects without however affecting their sterilization.

Guarantee of Maintaining the Initial Level of Disinfection/Sterilization of the MDs Over Time During their Storage by Avoiding any Kind of Contamination Medical objects disposed in the packaging material and sealed (after treatment) should remain sterile after their exposure to the afterglow during their storage before use. To ensure that the packaging material presents an effective antimicrobial barrier over time, Applicants have proceeded in the following way: polystyrene Petri dishes containing $10^7$ *B. atrophaeus* spores were put inside the above mentioned polyolefin polymer bags (one open end) and exposed to the afterglow under conditions (pressure, power, exposure time, . . . ) for allowing maximization of the UV radiation intensity in order to reach the sterility assurance level. Once the sterilization cycle was completed, Applicants have closed (thermally sealed) the bags containing a Petri dish, and kept them under non-protected conditions of temperature, light, humidity, dust for one month at a given location.

The Petri dishes exposed to the afterglow remained sterile when kept in the sealed bag for (at least) 1 month.

Toxicity of the BagLight™PolySilk™ Bags

According to the preceding results, the exposed and unexposed polyolefin polymer packaging material does not show any sporicidal or bactericidal activity. To check whether the packaging material could interfere with the growth of human cells, a toxicity evaluation of the bag with human cells was conducted by the Institut des Matériaux Industriels (IMI, Boucherville, Québec) of the National Research Council of Canada, according to the ISO protocol: ANSI/AAMI/ISO 10993:2003. The study conducted led to the conclusion that polyolefin polymer packaging material (BagLight™PolySilk™) exposed for 2 hours to the afterglow is non-toxic on human cells.

In view of the above-mentioned results, it can be said that the disinfection/sterilization method based on the use of the $N_2$—$O_2$ flowing afterglow provide several unusual advantages. This comes from the probable fact that, prior to the formation of excited NO, both N and O atoms penetrate into the packaging material. If the packaging material had been completely closed, there would have been a limited biocidal activity described as the so-called (UV photon) lamp effect. Indeed, with a germicidal lamp, it is impossible to reach locations which are not in its line of sight, as presumed from the fact that spore inactivation in a sealed package (although transparent to UV radiation) is less complete than if the package had been open. Post-sealing can thus take place upon return to atmospheric pressure. Such a sealing procedure thus prevents the situation in which an already sealed packaging material would collapse or stick to the object upon return to atmospheric pressure, due to the increased pressure. Furthermore, damage to the objects processed or treated with the packaging material was significantly less important than for those processed without packaging materials. This has been shown by the fact that the spores processed inside the packaging material for 120 min, showed minimal morphological modifications while they were seriously affected when exposed without the packaging material.

Moreover, when returning a sealed package to ambient air, at the time of using the object, as a result of the pressure difference, there could be an entry of contaminating species present in the ambient air, thus reducing the level of disinfection/sterility of the MD.

Consequently, the packaging material provides protection against outside contaminant species. It also ensures protection, during exposure to the afterglow, against damage to the medical devices including those fully made of polymers or having polymer components.

Metal Medical Devices (Forceps and Hemostatic Clamps)

Stainless steel MDs (forceps and hemostatic clamps) have been processed or treated without affecting the packaging material.

Preliminary tests with spores deposited on medical devices such as forceps and hemostatic clamps were carried out in the polyolefin polymer packaging material (for example BagLight™PolySilk™) exposed to the $N_2$—$O_2$ afterglow. The survival results are shown in Table 3.

TABLE 3 the number of survivors of ($10^6$) *B. atrophaeus* spores deposited on medical devices and exposed within the packaging material to $N_2$—$O_2$ afterglow.

| | Number of survivors Duration of exposure | |
|---|---|---|
| | 60 min | 120 min |
| Forceps | 56 ± 58 (n = 2) | 10 ± 10 (n = 3) |
| Hemostatic clamps | 249 ± 81 (n = 2) | Not available* | n is the number of exposed samples.

The results of Table 3 show that spores deposited on such medical devices seem more difficult to sterilize than if they had been in Petri dishes, probably due to the nature of the material and their configuration. After 120 minutes of exposure to the $N_2$—$O_2$ afterglow, the packaging material did not show any apparent change or damage.

Double Packaging

Double packaging corresponds to a second packing of the MDs, eventually performed outside the sterilization chamber. This second packaging material is to be removed at the time of entering, for instance, a room placed under sterile conditions. It ensures an additional protection of the first packaging and of its content.

It is to be noted that the individual polyolefin polymer packaging material (for example BagLight™PolySilk™) is currently delivered to customers inside another packaging material (thermally sealed) containing a group of packaging bags or pouches (e.g. 20-25 bags). Stored as such, the packaging bags or pouches are guaranteed sterile by the manufacturer for a period of 3 years.

Thermal Sealing

The thermal sealing of the polyolefin polymer packaging material (for example that of the BagLight™PolySilk™ packaging material) is very hermetic and sturdy. With the sealing device provided by the manufacturer of BagLight™PolySilk™ (sealing effected within a few seconds), it was found to be impossible with human hands to break open the sealed package.

Exposing MDs to an Argon Plasma Discharge

MDs were also exposed to an argon plasma discharge (direct contact with the discharge as opposed to a post-discharge). It was noted that the packaging material was damaged: it appeared more opaque and its UV transparency was reduced in the domain of the short wavelengths. In addition, the sterilization time was greatly increased with respect to that without packaging. Nevertheless, the packaging material remained very protective because spores exposed inside the package for 120 min appeared again without (external) morphological modifications using DAPI evaluation method (not shown).

Physical and Optical Characterization of the Bag

Macroscopic Observations

After 120 min of exposure to the $N_2$—$O_2$ afterglow, Applicants have observed that the polyolefin polymer packaging material did not emit any particular odor, that the surface was not damaged (no ripping) but that it felt rougher to the touch, which suggested a change in the surface properties. There was little change (less than 0.5%) in the weight of the bags after exposure. In addition, when filling the bag with water, Applicants did not observe any leak, which showed that it remained impervious after exposure. Incubation of the packaging at 56° C. for 48 hours did not alter its properties.

The Applicants have also used the same method to inactivate bacterial endospores using dry ozone. Putting the Petri dish on which *Geobacillus stearothermophilus* spores ATCC®7953 had been deposited into the polyolefin packaging material provided the same inactivation rate as if the Petri dish was without packaging. There were no apparent modifications of the material.

Spectral Response of the Packaging Material

UV radiation, without being bound to such a theory, is recognized as being one of the main mechanisms of inactivation of bacterial spores. The survival curves obtained (FIG. 4) for bacterial spores exposed or not exposed in a bag are identical. From this, Applicants deduced that the packaging material or bag had no influence on spore inactivation.

The percentage of UV transparency of the packaging material after its exposure to the afterglow compared to that of a non-exposed packaging material was obtained making use of an Oriel deuterium lamp, which emits a continuum radiation between 200 nm and 900 nm. Applicants recorded the continuum intensity emitted by the lamp and picked up by an optical fiber connected to a spectrometer (HR 320, photomultiplier R636). Then, Applicants successively put in front of the optical fiber a non-exposed bag (for example BagLight™PolySilk™), then a bag previously exposed for 120 min to the afterglow. The percentage of UV transparency (transmission) of the packaging material is then determined for a non-exposed bag and a 120-min exposed bag by calculating the ratio of the signal obtained with the corresponding bag over the continuum intensity recorded without any bag. The results are presented in FIG. 7 as ratios of the signal obtained with unexposed and exposed bag over the signal recorded without bag.

Figure 7:
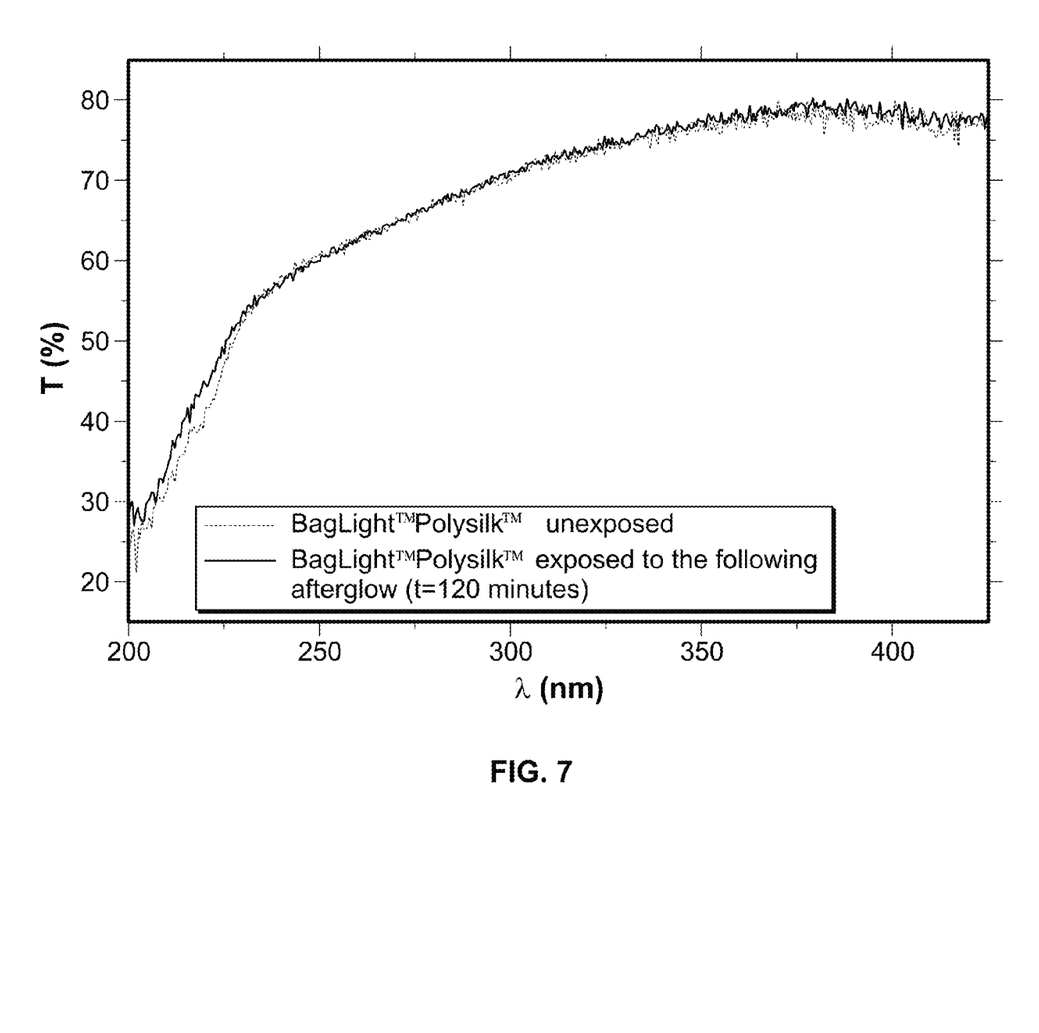
FIG. 7 shows the optical transmission for different wavelengths of non-exposed packaging material and of the same material exposed for 120 minutes to an $N_2$—$O_2$ flowing afterglow, according to an example of a method according to the present disclosure.

FIG. 7 shows, first of all, that the UV radiation transmission of the packaging material varies with the wavelength of the UV radiation. The transmission percentage at 200 nm is 25%, which increases rapidly up to 60% at 250 nm and then goes increasing moderately to yield approximately 80% at 400 nm. Applicants observed that the UV transparency of the packaging material exposed for 120 min to afterglow is identical to that of the non-exposed packaging material.

Angle of Contact

Applicants have shown (Table 2) a more important formation of the *S. aureus* biofilm on the packaging material after its exposure for 120 min to the $N_2$—$O_2$ afterglow. This indicates, without being bound to such an explanation, a modification of the bag surface energy.

Measurement of the angle of contact (measurement of the angle of a drop of water deposited on the surface of a material) usually enables one to evaluate the hydrophobicity/hydrophilicity of a surface. The more the drop of water expands over the surface, the smaller is the angle of contact and the more hydrophilic is the surface. This measurement allowed the Applicants to characterize and quantify the changes on the bag surface that occurred during the exposure to the $N_2$—$O_2$ afterglow as observed when it comes back to atmospheric pressure after the exposure.

Figure 8:
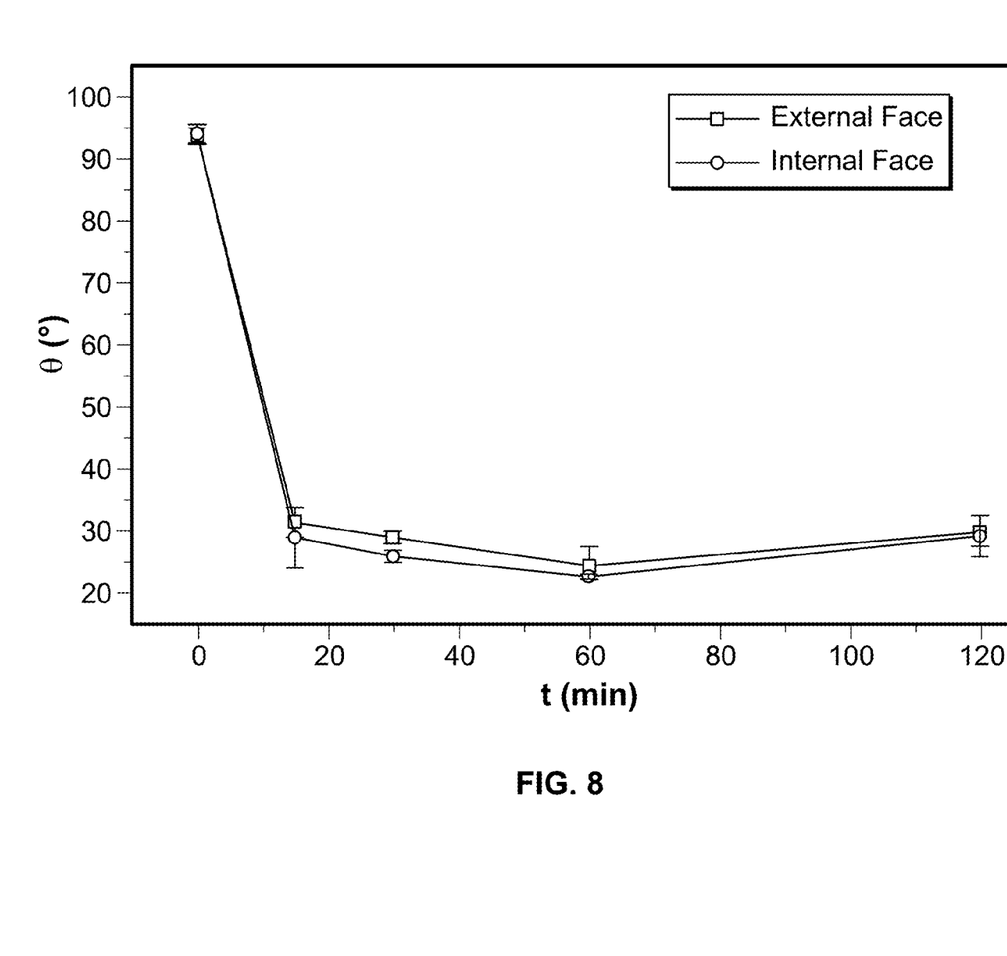
FIG. 8 shows measurement of the angle of contact of the inner and outer surfaces of a packaging material as functions of time of exposure to the $N_2$—$O_2$ afterglow, wherein the packaging material has been treated in accordance with an example of a method as described in the present disclosure.

FIG. 8 shows the values of the angle of contact, achieved with a deionized drop of water (from 2 μl to 3 μl), on the outer and inner surfaces of the packaging material after different times of exposure to the $N_2$—$O_2$ afterglow. The surfaces investigated were those that were not in contact with the bottom of the chamber. Applicants observed, on the one hand, that the surface of the non-exposed bag (t=0) was very hydrophobic since the angle of contact was θ=94° and, on the other hand, that the surface became very hydrophilic after 15 minutes of exposure to $N_2$—$O_2$ afterglow since the angle of contact decreased to a value between θ≈22° and θ≈29°. These observed variations are similar for both the outer and inner surfaces.

The interaction forces responsible for the observed angle of contact of the bag were quantified as the (microscopic) parameter γ that represents the surface free-energy. By using the angle of contact values obtained with deionized water and another liquid (in the present case glycerol) on the bag, it is possible to quantify the polar contribution $\gamma_S^p$ and the dispersive contribution $\gamma_S^d$ of the surface of the bag after different times of exposure to the afterglow. Total free energy $\gamma_S$ of the surface was expressed by the sum of these two components, namely $\gamma_S = \gamma_S^d + \gamma_S^p$ (D. K. Owens and R. C. Wendt, *Estimation of the surface free energy of polymers*, Journal of Applied Polymer Science vol. 13, pp. 1741-1747 (1969).

Figure 9:
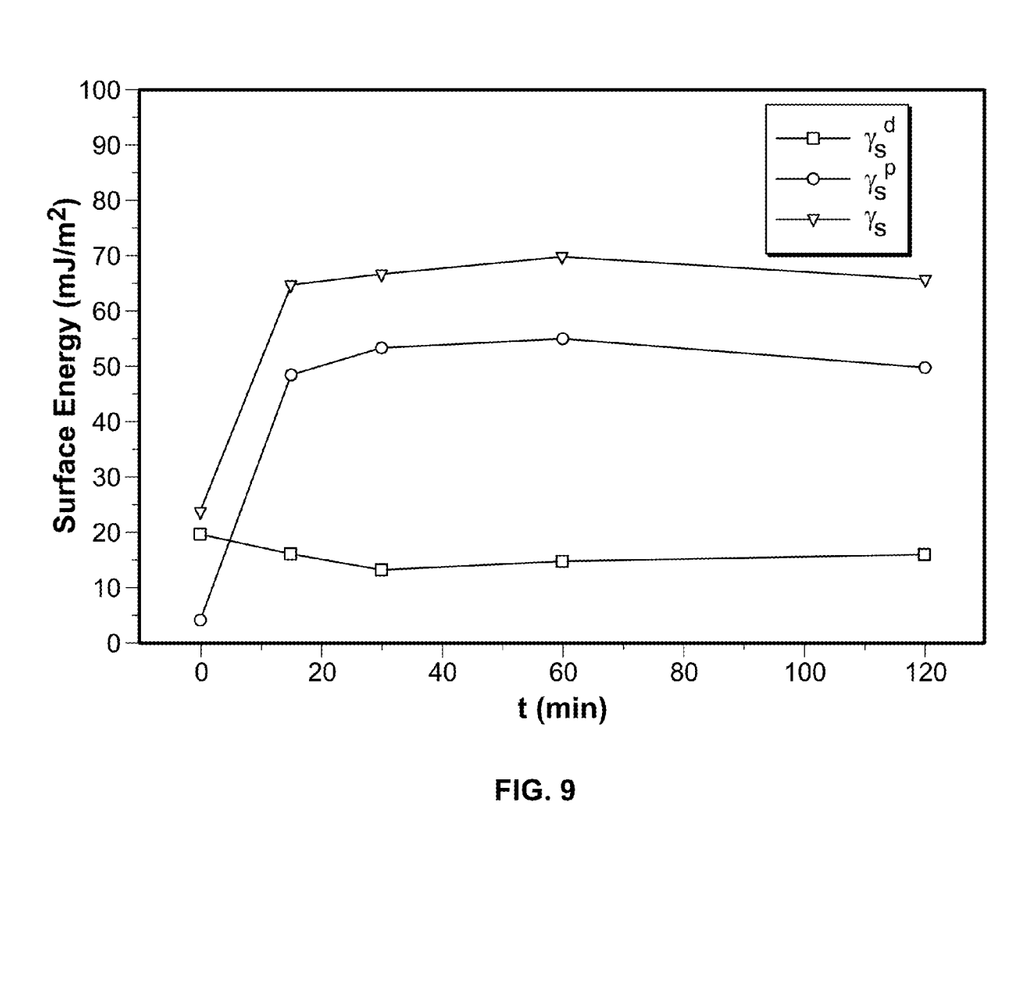
FIG. 9 shows the surface energy components determined from measurement of the angle of contact of the outer surface of a packaging material that was treated by an example of a method according to the present disclosure, as a function of the time of exposure to $N_2$—$O_2$ afterglow.

FIG. 9 shows that the forces of interaction at the surface of the non-exposed bag (t=0) are for the majority of the dispersive type ($\gamma_S^p \approx 5$ mJ/m$^2$<$\gamma_S^d \approx 20$ mJ/m$^2$). Applicants also observed that the forces of interaction at the surface of the bag after 15 minutes of exposure become for the majority of the polar type ($\gamma_S^d \approx 15$ mJ/m$^2$<$\gamma_S^p \approx 50$ mJ/m$^2$). These values remained valid thereafter irrespective of a longer time of exposure of the bag to the $N_2$—$O_2$ afterglow. This considerable increase of the polar contribution is, without being bound to such an explanation, most likely responsible for the increase of the biofilm formation by allowing a strong adherence of the *S. aureus* bacteria (T. J. Kinnari, et al., *Effect of surface roughness and sterilization on bacterial adherence to ultra-high molecular weight polyethylene*. Journal Compilation©2009 European Society of Clinical Microbiology and Infectious Diseases, CMI, 2009, 1-6)

It was thus shown that the methods of the present disclosure involve UV-transparent but non-porous packaging material that has at least one open end at the moment of exposure to the afterglow. From the extent of damage inflicted to spores exposed to the afterglow, it can be inferred that this packaging material should provide a greater protection to objects such as medical devices (MDs) processed in the $N_2$—$O_2$ afterglow without extending the time necessary to arrive at the disinfection/sterility level required. The packaging material can be sealed thermally after exposure to the post-discharge, once the enclosure or chamber has returned to atmospheric pressure (AP). The preservation time for keeping the MDs after thermal sealing appears higher than that of presently used porous packaging materials for other known sterilization methods.

Applicants have thus shown the valuable advantages of using non-porous materials as opposed to porous wrapping materials in the flowing afterglow sterilization process. This differs from the teaching of certain prior art documents, such as for example U.S. Pat. No. 4,321,232. This patent suggests that plasma processing requires porous types of packaging materials in order for the active, atomic and molecular species to penetrate them since the packaging is already sealed before the sterilization process. Several advantages are provided when using a non-porous packaging material in the context of the methods of the present disclosure. For instance, as previously mentioned, the non-porous polyolefin polymer packaging material (for example BagLight™PolySilk™), provides longer conservation time (under sterile conditions) of packaged MDs that have been processed than with porous packaging material. Furthermore, it has good resistance to afterglow processing exposure, which is not the case of certain packaging materials commonly used for sterilization. In addition, Applicants have demonstrated that the antimicrobial barrier property of a BagLight™PolySilk™ packaging material is preserved under the tested operating conditions.

As mentioned above, Applicants have requested investigation of the toxicity of the polyolefin polymer packaging material (internal and external part) subjected to afterglow, which indicated its non-toxicity on human cells, according to the ISO protocol: ANSI/AAMI/ISO 10993:2003.

It was found that the packaging material provided to the object to be treated a protection without however reducing the efficiency of the treatment in terms of sterilization.

In view of the above mentioned results, it can be said that the presented methods provided several advantages. First, they can allow, for example when using a mixture of $N_2$ and $O_2$ for generating the plasma, active species, prior to the formation of excited NO, both N and O atoms to penetrate into the packaging material. If the packaging material had been closed, there would have been a limited biocidal activity due to the so-called lamp effect. Indeed, it would have been impossible to reach locations that are not in the line of sight of the lamp (shown on a sealed package material: inactivation is less complete than if it had been open although the material is transparent to UV photons). Post-sealing or closing can thus take place upon return to atmospheric pressure. These methods thus prevent the situation in which the packaging material would have either blown up or collapsed/stuck to the object due to the pressure difference. Secondly, damage to the objects processed or treated with the packaging material could be considerably less important than for those processed without packaging material. This has been shown by the fact that the spores processed inside the packaging material for 120 min, showed up without (external) morphological modifications while they were seriously affected without the packaging material.

In addition, when returning a sealed package to ambient air at the time of using the object, as a result of the pressure difference, there could be an entry of contaminating species present in the ambient air, thus reducing the level of disinfection/sterility of the MDs. Once the sterilization process has been completed, the packaging material can be sealed at atmospheric pressure, making sure that a filter (for example a 0.22 micrometer filter) prevents contaminants from outside the chamber to contaminate the MDs. Synthetic air or even pure nitrogen can be used when returning to atmospheric pressure, prior to the sealing process.

The present disclosure has been described with regard to specific examples. The description was intended to help the understanding of the present disclosure, rather than to limit its scope. It will be apparent to one skilled in the art that various modifications may be made to the present disclosure without departing from the scope of the present disclosure as described herein, and such modifications are intended to be covered by the present document. More particularly, the person skilled in the art would understand that various other packaging materials could be used for the methods described in the present disclosure and that the packaging material could be used with various other plasma sterilization systems.

REFERENCES

J. F. Gardner and M. M. Peel, *Introduction to Sterilization, Disinfection and Infection Control*. Churchill Livingstone, Melbourne Edinburgh London Tokyo and New York 1991.
P. Setlow, Spores of *Bacillus subtilis*: their resistance to and killing by radiation, heat and chemicals. Journal of Applied Microbiology 101 (2006) 514-525
Munakata, M., M. Saito, and K. Hieda, *Inactivation action spectra of Bacillus subtilis spores in extended ultraviolet wavelengths (50-300 nm) obtained with synchrotron radiation*. Photochemistry and Photobiology 1991. 54(5): p. 761-768.
DAPI, Product Information, SIGMA-ALDRICH
Also: Authors: Analysis of dye binding by membrane potential in spores of *Bacillus* species, Journal of Applied Microbiology, 106, 814-824 (2009)
D. K. Owens and R. C. Wendt, *Estimation of the surface free energy of polymers*, Journal of Applied Polymer Science vol. 13, pp. 1741-1747 (1969)
T. J. Kinnari, et al., *Effect of surface roughness and sterilization on bacterial adherence to ultra-high molecular weight polyethylene*. Journal Compilation©2009 European Society of Clinical Microbiology and Infectious Diseases, CMI, 2009, 1-6

The invention claimed is:

1. A method for sterilizing and/or disinfecting an object comprising exposing said object disposed in a packaging material having at least one open end or at least one portion defining an aperture, to an afterglow plasma, said packaging material being non-porous and being transparent to UV radiation,
wherein said method is carried out by:
measuring at least one of UV emission intensity and optical absorption to determine the population density of species emitting UV photons in the chamber as a function of gas pressure and gas flow rate to determine operating conditions that maximize UV radiation intensity and that maximizes the presence of UV photon emitting species in the chamber; and
applying said operating conditions in the chamber that maximizes UV radiation intensity and that maximizes the presence of UV photon emitting species in the chamber.

2. The method of claim 1, wherein said packaging material is adapted to maintain at least 95% of its non-porosity and transparency to UV radiation after exposure to said afterglow.

3. The method of claim 2, wherein said packaging material is impervious to bacteria and wherein said packaging material is adapted to maintain at least 95% of its imperviousness to bacteria after exposure to said afterglow.

4. The method of claim 1, wherein said packaging material comprises a polyolefin polymer.

5. The method of claim 1, wherein said packaging material comprises a polyethylene-based polymer.

6. The method of claim 1, wherein said plasma is produced by subjecting a gas to an electric field, said gas comprising $N_2$ and $O_2$.

7. The method of claim 6, wherein said method is carried out with a power absorbed by the plasma source P (W) referred to the afterglow chamber volume V (L) of about P/V of 2 to about 40 W/L.

8. The method of claim 6 wherein said method is carried out by maximizing intensity of UV radiation emanating from the $NO_\gamma$ molecular system having a spectral domain of about 205 nm to about 290 nm.

9. The method of claim 1, wherein said afterglow plasma is ozone generated by a corona discharge consisting essentially of $O_2$.

10. A method for using a packaging material, said method comprising:
disposing an object to be sterilized into said packaging material, said packaging material being non-porous, transparent to UV radiation, and having at least one open end or at least one portion defining an aperture; and
exposing said object and said packaging material to an afterglow of a plasma, thereby protecting said object to be sterilized,
wherein said method is carried out in a sterilizer and wherein after exposure to said afterglow plasma and before opening said sterilizer, said at least one open end or said aperture of said at least one portion is closed.

11. The method of claim 10, wherein said packaging material is a pouch or a bag having said at least one open end.

12. The method of claim 10 wherein said method is carried out by:
measuring at least one of UV emission intensity and optical absorption to determine the population density of species emitting UV photons in the chamber as a function of gas pressure to determine a gas pressure that maximizes UV radiation intensity and that maximizes the presence of UV photon emitting species in the chamber; and
measuring at least one of UV emission intensity and optical absorption to determine the population density of species emitting UV photons in the chamber as a function of stream flow rate to determine a flow rate that maximizes UV radiation intensity and that maximizes the presence of UV photon emitting species in the chamber; and
applying the stream at a flow rate and a gas pressure in the chamber that maximizes UV radiation intensity and that maximizes the presence of UV photon emitting species in the chamber.

13. The method of claim 10, wherein said method is carried by maintaining the temperature of said object at a temperature below 45° C.

14. The method of claim 10, wherein said packaging material comprises a single open end that is disposed, in a sterilizer, in such a manner to be opposed to a plasma source or plasma inlet of said sterilizer.

15. A method for using a packaging material, said method comprising:
inserting an object to be sterilized into said packaging material, said packaging material comprising a polyolefin polymer and being non-porous, transparent to UV radiation, and having at least one open end or at least one portion defining an aperture; and
exposing said object and said packaging material to an afterglow of a plasma produced by subjecting a gas comprising $N_2$ and $O_2$ to an electric field, thereby protecting said object to be sterilized without significantly reducing efficiency of sterilization as compared to a same treatment carried out outside of said packaging material, wherein said method is carried out by maximizing intensity of UV radiation emanating from the $NO_\gamma$ molecular system having a spectral domain of about 205 nm to about 290 nm.

16. The method of claim 15, wherein said polyolefin polymer comprises polymerized ethylene monomers, polymerized propylene monomers, or a mixture thereof.

17. The method of claim 15, wherein said gas comprises about 0.1 to about 2% of $O_2$.

18. The method of claim 15 wherein said method is carried out by:
   measuring at least one of UV emission intensity and optical absorption to determine the population density of species emitting UV photons in the chamber as a function of power density P/V to determine operating conditions that maximize UV radiation intensity and that maximizes the presence of UV photon emitting species in the chamber; and
   applying said operating conditions in the chamber that maximizes UV radiation intensity and that maximizes the presence of UV photon emitting species in the chamber.

19. The method of claim 15, wherein said method is carried out in a sterilizer and wherein after exposure to said afterglow plasma and before opening said sterilizer, said at least one open end or said aperture of said at least one portion is closed.

* * * * *